United States Patent [19]

Groke

[11] Patent Number: 5,554,618
[45] Date of Patent: Sep. 10, 1996

[54] INTRAVENOUSLY ADMINISTRABLE AQUEOUS SOLUTION

[75] Inventor: Karl Groke, Eggersdorf, Austria

[73] Assignee: Hafslund Nycomed Pharma Aktiengesellschaft, Linz, Austria

[21] Appl. No.: 305,605

[22] Filed: Sep. 14, 1994

[30] Foreign Application Priority Data

Sep. 14, 1993 [DE] Germany ............... 43 31 147.4

[51] Int. Cl.⁶ ............... A61K 31/19; A61K 31/195; A61K 31/425; A61K 31/505
[52] U.S. Cl. ............... 514/275; 514/362; 514/561; 514/574
[58] Field of Search ............... 514/362, 275, 514/561, 574

[56] References Cited

U.S. PATENT DOCUMENTS

| 4,327,084 | 4/1982 | Groke | 424/176 |
| 4,732,915 | 3/1988 | Ayer et al. | 514/567 |

OTHER PUBLICATIONS

Chemical Abstracts CA98:149586 (1982).

Primary Examiner—Phyllis G. Spivack
Attorney, Agent, or Firm—Wenderoth, Lind & Ponack

[57] ABSTRACT

An intravenously administrable, aqueous solution of a water-soluble, physiologically tolerable salt of sulfametrole and of trimethoprim, in which malic acid, L-serine and/or L-threonine are present as solubilizers, and which has a pH of of 6.5–7.0 is disclosed.

1 Claim, No Drawings

INTRAVENOUSLY ADMINISTRABLE AQUEOUS SOLUTION

The present invention relates to an intravenously administrable, aqueous solution of the sulfonamide 3-methoxy-4-(4'-benzenesulfonamido)-1,2,5-thiadiazole (sulfametrole) and of the sulfonamide potentiator 2,4-diamino- 5-(3',4',5'-trimethoxybenzyl)pyrimidine (trimethoprim), which has a pH in the range 6.4–7.2, can be sterilized in a customary manner and is distinguished by a good storage stability.

It is known that the combinations of sulfonamides with the sulfonamide potentiator trimethoprim, which are well established in therapy, cause great difficulties in conversion to parenterally tolerable solutions. These were especially to be attributed to the fact that the sulfonamides employed for such combinations, such as, inter alia, sulfametrole in alkaline medium, e.g. in the case of the sulfametrole at a pH of 7.4 and higher, form readily water-soluble salts, e.g. Na salts, but the weak base trimethoprim is already present as the free base in the alkaline range and is not soluble in water in this form. In the acid range, on the other hand, trimethoprim goes into solution with the formation of acid addition salts, but the sulfonamides under consideration are not soluble in water at the pH required. Only one way out is therefore open, to employ an organic solvent for one of the two constituents of the combination to obtain a solution (AT Patent 270,869, DE-A 2 400 218).

AT Patent 270,869 has disclosed readily tolerable, intravenously administrable, aqueous solutions of sulfametrole and trimethoprim having a pH of 7.4, in which the sulfametrole is employed as a salt with a strong counter-electrolyte, in particular NaOH, while the trimethoprim is brought into solution by addition of sugar alcohols, such as sorbitol, xylitol or mannitol, or of reducing sugars, such as fructose or glucose, as solubilizers.

One embodiment of these solutions having a pH of 7.4 and containing the sugar alcohol sorbitol as a solubilizer found widespread application in practice.

Owing to the situation that sugar alcohols and fructose may no longer be employed in parenterally administrable solutions in some countries, as a result of which the use of these substances as solubilizers is also affected, and owing to the difficulty that the sterilization of solutions containing trimethoprim and glucose causes, it was the object to find a novel, physiologically tolerable solubilizer for trimethoprim which enables the preparation of aqueous solutions of the combination sulfametrole-trimethoprim having a slightly alkaline reaction and containing the sulfametrole dissolved as the alkali metal salt.

In the context of investigations relating to this it has been possible to find that various α-hydroxymonocarboxylic acids and -dicarboxylic acids and also the amino acids L-serin and L-threonine display solubilizing properties in a slightly alkaline medium at pH 7.5 and more. The clear solutions thus produced, however, prove only to be metastable; after storage times which were too short in practice it was possible to record crystallization of trimethoprim.

Surprisingly it has now been possible to find that solutions of this type are stable in a very restricted, weakly acidic to neutral pH range, namely from 6.4 to 7.2, and precipitation or crystallization neither of sulfametrole, nor of trimethoprim, is to be noted if malic acid, serine or threonine or mixtures of these acids are used as solubilizers. If this pH range is left, only metastable solutions are obtained which at pHs above 7.2 contain precipitates of trimethoprim and below 6.4 those of sulfametrole.

The present invention accordingly relates to an intravenously administrable, aqueous solution of the sulfonamide sulfametrole present as a salt and of trimethoprim, which is characterized in that it contains malic acid, L-serin and/or L-threonine as a solubilizer for the trimethoprim, together with a strong, physiologically tolerable base forming water-soluble salts with the sulfonamide and the malic acid in an amount equimolar to the amount of sulfonamide present and also in an amount of approximately 2 mol per mole of malic acid present, the pH of the solution being adjusted to the range 6.4–7.2.

While it was primarily endeavored by consideration up to now to incorporate into the solution sufficient alkali to ensure that at least 1 mol of the strong counter-base was available per mole of sulfametrole and therefore a pH clearly lying in the alkaline range was preferred, according to the present invention at most a pH of 7.2 is tolerated. It is even preferred that the pH does not exceed the neutral point, but rather remains in the weakly acidic range. The pH preferably to be set is 6.5–7.0.

Among the acids having a solubilizing action according to the present invention, malic acid is in this case to be given preference, as in this embodiment of the solution according to the invention not only that amount of counter-base, preferably NaOH, is present which is equivalent to the available amount of sulfametrole. On the contrary, a further amount of counter-base which is approximately equivalent to the amount of malic acid present is additionally needed. As it is paramount in this case that the pH limit of 7.2, preferably 7.0, must not be exceeded, this means that the amount of counter-base has to remain in a small excess in relation to the malic acid. The fact that in this case, nevertheless, no instability of the salt of sulfametrole at this slightly acidic pH occurs which would be revealed by a withdrawal of alkali by the malic acid is to be attributed to the fact that the second dissociation constant of $1.39 \times 10^{-5}$ is lower than the second dissociation step of sulfametrole (dissociation constant $1.6 \times 10^{-5}$) and the salt of malic acid present, even when its second step is not completely neutralized, is an alkali reserve for sulfametrole, which imparts stability to the solution.

This effect is not obtained with acids having a relatively strong second dissociation step. The consequence would then be a withdrawal of alkali in the case of sulfametrole and an instability associated therewith which has been avoided according to a previous school of thought by a more strongly alkaline pH of the solution which, however, leads to instabilities in the case of trimethoprim.

If the amino acids L-serine and/or L-threonine are employed as solubilizers, these alkali reserves do not exist, but the danger of a withdrawal of base by these solubilizers is likewise not to be expected as they are ampholytes and do not need any counter-base for the ionization of the carboxyl group. In this case, the solution only requires the amount of counter-based equivalent to the sulfametrole and a small excess of this base for adjusting the pH, depending on how this is selected within the range according to the invention.

The solubilizing effect of the three acids employed according to the invention on the trimethoprim is very marked, especially in the range according to the invention. To safely obtain a solution which is also stable on storage over a relatively long time, it is recommended to set in this solution a content of 100 milli-equivalents of the solubilizer per liter of solution, that is 50 mmol/l with malic acid and 100 mmol/l with L-serine and L-threonine. This concentration, however, is only a minimum amount which can be increased without problems and also should be increased in order to obtain optimum results. An upper limit in the case of the use of malic acid, apart from economic considerations, is specified, however, in that the content of the strong base employed as a counterion in the daily dose must remain within physiologically tolerable limits. Thus, e.g. the daily requirement of a patient for sodium is 240 mmol, an amount which should not be substantially exceeded for physiological reasons, as a result of which an upper limit results for the use of malic acid if it is neutralized with NaOH. Since, however, the solubilizing properties of the malic acid are optimum even at concentrations barely above the minimum concentration mentioned as expedient, in practice there is no danger that an exceeding of the tolerable amount of sodium could occur. In the case of the potassium ion, the physiologically tolerable daily dose, on the other hand, is so low that use of KOH on its own as a counter-base for malic acid is not to be taken into consideration.

As a rule, 400 mmol of Na ion per liter of the solution according to the invention should not be exceeded in order to enable a sufficiently rapid infusion rate. This amount corresponds to the use of about 190 mmol of malic acid. High amounts of this type are, however, not necessary at all to achieve an optimum effect. The preferred amount of L-malic acid is 120–180 milliequivalents or 60–90 mmol/liter, where L-malic acid is to be preferred for physiological reasons.

If, on the other hand, the amino acids serin and/or threonine are used as solubilizers, the amount of counter-base required, as already said above, is very much lower. Even in this case, NaOH has proven very suitable for neutralization, here only of the sulfametrole, but it is also possible to employ KOH on its own, as the concentration of sulfametrole per liter of the solution is kept so low in practice that the tolerable amount of potassium ion is not exceeded. In the case of the solution previously employed in practice, the concentration of sulfametrole is 11.17 mmol/liter, and that of trimethoprim is 2.2 mmol/liter.

When using these two amino acids, an upper concentration limit would thus not be given with respect to the amount of Na or K ion compulsorily to be administered therewith. However, it is to be taken into account that excessively high administration rates of these two amino acids, which are not necessary at all for technical reasons, could lead to amino acid imbalances, especially when only one of the two amino acids is employed on its own. It may therefore be advantageous to employ these acids in a mixture, e.g. in a molar ratio of serin to threonine of 1:1 to 2:1, a molar ratio of 2:1 being preferred. For the same reason it may also be advantageous to combine one of the two amino acids with malic acid, as a result of which amino acid imbalances are not to be feared and the sodium burden can also be decreased compared with the use of malic acid on its own. Since malic acid, serin and threonine require the same administration rate in milliequivalents, this remains identical irrespective of whether individual acids or acid mixtures are employed.

For physiological reasons, the solutions according to the invention which, of course, are administered intravenously should be approximately isotonic, but at least have ⅔ isotonicity. When using malic acid as a solubilizer, solutions whose osmolarity is suitable are already obtained without assistance at doses which are clearly above the minimum dose, owing to the necessity of employing equivalent amounts of a counterion. At doses in the vicinity of the minimum dose, an osmolarity of approximately 200 mosmol/l is not achieved, however, so that the addition of osmotically active, inert constituents is indicated. Additionally, the osmolarity establishing itself in solutions according to the invention for whose preparation L-serine and/or L-threonine are used is not sufficient to be able to administer these solutions in an acceptable manner intravenously. Glycerol, especially, has proven suitable as an inert substance for adjusting the osmolarity. Especially in solutions which contain the aminohydroxycarboxylic acids, the osmolarity can also be adjusted to physiologically tolerable values by addition of sodium chloride, as such solutions do not have a high burden of sodium. When using malic acid as a solubilizer, the total Na burden is to be borne in mind when using sodium chloride for the purpose of adjusting the osmolarity.

For preparation of the solution according to the invention, the mono salt of sulfametrole is first prepared in an initially introduced amount of water which corresponds to somewhat less than the final volume using a strong, physiologically tolerable base to which either malic acid, together with approximately also double the amount likewise of a strong, physiologically tolerable base, or else L-serine and/or L-threonine is then added. The trimethoprim is introduced into the resulting, clear solution. Dissolution thereof is possible even at room temperature, but for acceleration it is recommended to work at elevated temperature, which can be up to approximately 90° C., where a temperature of 70° C. to 80° C. is to be preferred. The pH in the solution thus obtained must then be adjusted to the desired value within the range from 6.4 to 7.2. In this case, the addition of NaOH and/or KOH, preferably NaOH, is used to increase the pH. Should a reduction in the pH prove necessary, it is advisable to employ malic acid as the acid. The use of strong mineral acids, such as, for example, hydrochloric acid, could lead to instability of the solution.

It is particularly preferred in the preparation of the solution according to the invention to employ somewhat less than the equivalent amount of the strong counter-base, where the deficit is expediently to be selected such that the pH in each case comes to lie above 6, preferably at about 6.2 to 6.3. After dissolution of the trimethoprim, the fine adjustment of the pH is then carried out, at best with NaOH. If necessary, additives are then added to raise the osmolarity, after which the final volume of the solution is then set using water for infusion. A particular advantage of the solutions according to the invention is that they can be sterilized in an autoclave at customary temperatures, e.g. at 115° C. They remain stable for a relatively long time on storage both at 4° C. and at 10° C.

When choosing the pH within the range from 6.4–7.2 in the course of the preparation of the solution according to the invention, it is to be taken into account that during the sterilization slight pH shifts to higher values can occur. These shifts are, if starting from a pH of below 7, only a few hundredths, but become larger if the starting pH is above 7. Thus, e.g. at a starting pH of 7.17, increases of around approximately one tenth were observed, which represents an exceeding of the upper limit of 7.2. For this reason, it is recommended to adjust the pH before sterilization such that an exceeding of this type can be excluded during the sterilization.

The solution according to the invention is employed for the control of infections, the daily dose advantageously being 1.6 g of sulfametrole and 320 mg of trimethoprim, dissolved in 0.5 l of water. A solution is preferred which, per liter, contains 11.17 mmol of an Na salt of sulfametrole, 2.20 mmol of trimethoprim, 140–180 milliequivalents of L-malic acid, L-serine or L-threonine or the same equivalent amount of mixtures thereof, and the amounts of NaOH necessary for adjusting the pH to a value of 6.5–7.0, if appropriate in addition to inert additives for adjusting the osmolarity to physiologically tolerable values.

EXAMPLE 1

11.17 mmol=3.200 g of sulfametrole and 11.17 mmol=0.447 g of NaOH are dissolved in approximately 900 ml of water for infusion to give a clear solution. 70 mmol=9.38 g of L-malic acid are added together with 5.5 g of NaOH and dissolved. In the clear solution thus obtained, 640 mg of trimethoprim are dissolved with warming to 75° C. After cooling, 5 g of glycerol are added to raise the osmolarity, and the solution is brought to a volume of approximately 995 ml using water for infusion. The pH of the solution is then 6.25. It is raised to 7.09 by addition of 3.05 ml of 1M NaOH, after which the solution is then sterilized in the customary manner after making up to the final volume.

It has an osmolarity of 228 mosmol/l and shows no proneness to crystallization whatsoever on storage at 4° C. for 4 months.

EXAMPLE 2

Sulfametrole, malic acid, NaOH and trimethoprim are processed, as described in Example 1, to give a solution, only with the difference that, instead of 5.50 g of NaOH, 5.603 g of NaOH are added for neutralization of the malic acid. After addition of 5 g of glycerol and making up to 995 ml, the pH of the solution is 7.64. It is lowered to 6.64 by addition of 1.1 mmol of malic acid, after which the solution is finished as described in Example 1.

EXAMPLE 3

A solution is prepared as described in Example 1, only with the difference that for fine adjustment of the pH 0.9 ml of 1M NaOH is used. After making up to 1000 ml, a pH of 6.47 results. This solution is finished as described in Example 1. It shows no crystallization phenomena whatsoever on storage for 4 months.

EXAMPLE 4

11.17 mmol=3.20 g of sulfametrole are brought into solution in 900 ml of water with addition of 11.50 mmol=0.46 g of NaOH. 80 mmol=8.4 g of L-serine and 40 mmol=4.76 g of L-threonine are introduced into this solution and dissolved. 640 mg of trimethoprim are suspended in this solution and dissolved with warming to 70° C. The pH of the solution thus resulting is 7.03; it is not corrected. After addition of 65 mmol of NaCl for adjustment of the osmolarity, the solution is made up to the final volume of 1000 ml and sterilized in a customary manner.

The resulting solution has an osmolarity of 275 mosmol/l. It is stable on storage at 4° C. for a storage time of 4 months.

What I claim is:

1. An intravenously administrable, aqueous solution, comprising, per liter, 11.17 mmol of an Na salt of 3-methoxy-4-(4'-aminobenzenesulfonamido)-1,2,5-thiadiazole, 2.20 mmol of 2,4-diamino-5-(3',4',5'-trimethoxybenzyl)pyrimidine, 140–180 milliequivalents of L-malic acid or salt thereof, L-serine or L-threonine or the same equivalent amount of mixtures thereof, an amount of NaOH necessary for setting a pH of 6.5 to 7.0, and optionally inert additives for adjusting the osmolarity to physiologically tolerable values.

* * * * *